(12) United States Patent
Golz-Berner et al.

(10) Patent No.: US 6,989,150 B1
(45) Date of Patent: Jan. 24, 2006

(54) COSMETIC PREPARATION OF ACTIVE SUBSTANCES WITH A SYNERGISTICALLY INCREASED RADICAL PROTECTION FACTOR

(75) Inventors: Karin Golz-Berner, Monaco (DE); Leonhard Zastrow, Monaco (DE)

(73) Assignee: COTY B.V., (NL)

( * ) Notice: Subject to any disclaimer, the term of this patent is extended or adjusted under 35 U.S.C. 154(b) by 0 days.

(21) Appl. No.: 10/049,770

(22) PCT Filed: Oct. 8, 1999

(86) PCT No.: PCT/DE99/03295

§ 371 (c)(1),
(2), (4) Date: Feb. 19, 2002

(87) PCT Pub. No.: WO01/23832

PCT Pub. Date: Apr. 5, 2001

(51) Int. Cl.
*A61K 9/68* (2006.01)
*A61K 7/26* (2006.01)
*A61K 31/74* (2006.01)

(52) U.S. Cl. .......................... 424/401; 424/48; 424/58; 424/59; 424/78.03; 424/78.05; 424/78.1; 424/94.1; 424/440; 424/450; 424/451; 424/452; 424/725; 424/729; 424/736; 424/774; 424/775; 424/777

(58) Field of Classification Search ............. 424/78.03, 424/78.06, 46, 48, 58, 59, 78.1, 94.1, 440, 424/450, 451, 452, 725, 729, 736, 775, 777, 424/401, 78.05, 774–5
See application file for complete search history.

(56) References Cited

U.S. PATENT DOCUMENTS

| | | | |
|---|---|---|---|
| 5,552,378 A | | 9/1996 | Trinh et al. |
| 5,629,185 A | | 5/1997 | Stanzl et al. |
| 5,639,473 A | * | 6/1997 | Grinstaff et al. ............ 424/450 |
| 5,674,912 A | * | 10/1997 | Martin ....................... 514/724 |
| 6,235,315 B1 | * | 5/2001 | Runge et al. ................ 424/489 |
| 6,258,377 B1 | * | 7/2001 | New et al. ................... 424/450 |
| 6,309,627 B1 | * | 10/2001 | Golz-Berner et al. ......... 424/59 |
| 6,426,080 B1 | * | 7/2002 | Golz-Berner et al. ....... 424/401 |
| 6,843,995 B2 | * | 1/2005 | Golz-Berner et al. .. 424/195.15 |

FOREIGN PATENT DOCUMENTS

| | | |
|---|---|---|
| DE | 43 28 639 A1 | 3/1995 |
| FR | 2 762 008 | 4/1997 |
| FR | 2 770 228 | 4/1999 |
| GB | 2 237 805 A | 5/1991 |
| WO | WO 97/45100 | 12/1997 |

* cited by examiner

*Primary Examiner*—Herbert J. Lilling
(74) *Attorney, Agent, or Firm*—Pendorf & Cutliff

(57) ABSTRACT

The inventive cosmetic preparation of active substances, as such as well as in combination with other active substances, protects the skin against free radical aggression in a particularly effective manner. The preparation consists of a bark extract of *quebracho blanco* which contains at least 90 wt. % of proanthocyanidine oligomers, a silkworm extract which contains the peptide cecropine, amino acids and a vitamin mixture, a non-ionic, cationic or anionic hydro-gel, phopholipids, a yeast disintegration product and cyclodextrines. The inventive preparation can contain additional active substances such as plant extracts of acerola, sea weed, citrus, bitter orange, cherry, papaya, tea, coffee beans, skin tree and angelica. The preparations have synergistically increased radical protection factors of up to 10,000. Cosmetic compositions containing said preparations have radical protection factors of between 40 and 400 according to the portion of the preparation.

12 Claims, No Drawings

COSMETIC PREPARATION OF ACTIVE SUBSTANCES WITH A SYNERGISTICALLY INCREASED RADICAL PROTECTION FACTOR

The inventive cosmetic preparation, as such as well as in combination with other active substances, protects the skin in a particularly effective way against free radical aggression.

Free radicals such as superoxide ions, hydroxy radicals, oxides are known as a major factor of degeneration and thus the ageing of the skin. They destruct the proteins and lipids of the cellular membrane, affect the DNA and also decompose the hyaluronic acid, a key substance of the skin. Under normal biological conditions there is an equilibrium ratio between the free radicals coming up and their embankment by endogenous chemical or enzymatic systems. Additional outside stress factors such as aggressive atmosphere, tobacco smoke, ultraviolet radiation etc. may overload these inherent immune systems and shift the equilibrium in favour of the free radicals. Inflammation or ageing phenomena of the skin may occur, indicating a need for compensation by cosmetic products.

There has already been proposed a series of products for this purpose, most of them containing mixtures of the vitamins A, C and E or additives of superoxide dismutase or extracts of certain plants or animals. Thus a cosmetic compound containing ultrasound decomposition products of yeast and other cellular dispersions is known from U.S. Pat. No. 5,629,185. From WO96/29048 a cosmetic containing condensed decomposition products of plants or animals is known. There is also a number of publications describing the use of pure plant extracts for cosmetic purposes, such as WO97/45100, where a mixture of seven different extracts is described for anti-cellulite treatment.

The search for other effective substances is a major element of cosmetic research. Another problem of many of these products is that the substances which are effective against free radicals often do not keep their scavenging properties within the ready cosmetic compound, i.e. it requires special formulations to permanently maintain the effectiveness of the radical scavengers.

The use of cyclodextrins in cosmetic products in order to slowly release active substances or to conceal bodily odours is know from U.S. Pat. No. 5,552,378 and other patents.

On the other hand it seems that it has not become widely known in the cosmetic industry yet that there is a possibility of measuring the antioxidant potential of the skin (DE 4328639) and recently also of determining the radical protection coefficient of a cosmetic preparation by using a relatively simple method and to purposefully add materials to such a preparation.

It is an object of the present invention to provide a cosmetic preparation of active substances which has a particularly high radical protection potential without addition of further active substances with radical scavenging properties.

Another objective of the invention is to provide a preparation of active substances that keeps its radical protection potential over a long period of time and especially such preparations of active substances which achieve further improvement of properties, in particular with regard to opening the pores of the skin.

According to the invention, the cosmetic preparation of active substances with a high radical protection factor is characterised by comprising (a) a product obtained by extraction of the bark of Ouebracho blanco and subsequent enzymatic hydrolysis, containing at least 90 percent by weight of proanthocyanidine oligomers and up to 10 percent by weight of gallic acid, wherein the content of (a), which is available in a concentration of 2 percent by weight linked to a microcapsules, ranges from 0.1 to 10 percent by weight;

(b) an extract of the silkworm obtained by extraction, containing the peptide Cecropine, amino acids and a vitamin mix, wherein the content of (b) may range from 0.1 to 10 percent by weight;

(c) a non-ionic, cationic or anionic hydrogel or mixture of hydrogels, wherein the content of (c) may range from 0.1 to 5 percent by weight; (d) one or several phospholipids comprising 0.1 up to 30 percent by weight;

(e) an ultrasound decomposition product of a yeast containing at least 150 units of superoxide dismutase per ml, wherein the content of the decomposition product is in the range from 0.5 to 4 percent by weight;

(f) one or more cyclodextrins selected from the group consisting of β- and γ-cyclodextrins with a share of 0.5 to 8% by weight; and (g) up to 100 percent by weight of water;

related to the total weight of the active substance preparation each.

Optionally the active substance preparation comprises an extract of acerola fruits *Malpighia punidifolia*, wherein the content of that is in the range from 1 to 20 percent by weight.

The Quebracho bark extract according to the invention or its hydrolysis product has a very high portion of proanthocyanidines representing condensed tannins. These compounds appearing as oligomers and the low portion of gallic acid in this combination and in a concentration between 1 and 10 percent by weight shows a clear radical protection effect, which by far exceeds the effect of superoxide dismutase (SOD). The activity against free radicals was compared with that of SOD and found to be 42% for a 1 percent by weight solution of the extract (SOD 4%), 83% for a 2.5% by weight solution (SOD 15%) and 100% for a 5% by weight solution (SOD 38%).

Preferably the extract (a) contains at least 95 percent by weight of proanthocyanidine oligomers and up to 5 percent by weight of gallic acid, in particular at least 99 percent by weight of proanthocyanidine oligomers and up to 1 percent by weight of gallic acid.

The content of (a) is 1 to 10 percent by weight, wherein the active substance from the Quebracho bark is enclosed in microcapsules. The microcapsules may consist of petrolatum, sodium tristearat, agar, phenonip and water.

The silkworm extract (b) is obtained by extraction of the silkworm (*Bombyx mori*) with 1,2-propylene glycol and contains vitamins, amino acids and the Cecropine peptide, which has a special antibacterial functionality. A range of studies of the haemolymph and the cuticular matrix of the silkworm carried out during the last years showed that it does not only contain antibacterial peptides but also inhibitors, in particular fungal protease inhibitors. Such extracts also show oxygen-consuming properties, thus activating the cellular metabolism, and they have moisture-keeping properties, a clear curative effect on lesions in the skin by reducing healing time and a skin-smoothing effect.

Preferably, the extract (b) includes the amino acids aspartic acid, asparagine, threonine, serine, glutaminic acid, proline, glycine, alanine, valine, cysteine, methionine, isoleucine, leucine, tyrosine, phenylalanine, lysine, histidine, arginine.

Preferably extract (b) also contains a vitamin mixture including vitamins $B_1$, $B_2$, $B_5$, $B_6$, $B_8$, $B_9$, $B_{12}$, PP, A, E and C.

The concentration of components (a) and (b) in the active substance preparation preferably ranges from 0.1 to 3 percent by weight each, in particular from 0.5 to 3 percent by weight.

The gel contained according to the invention, which may also be a mixture of different gels, is a hydrogel soluble in water at temperatures above 40 up to 50° C., approximately, and which takes the gel structure at low temperatures between 10 and 30° C. Examples of such gels are non-ionic polymers such as polyvinyl alcohol, polyvinyl pyrrolidone-modified maize starch and hydroxyethylcellulose, cationic polymers such as cationic Guar, cationic cellulose, synthetic cationic polymers or gels such as gelatine, carrageenan, bentonite gels, copolymeric gels such as carbomer.

The phospholipids contained according to the invention have been selected among phosphatidyl choline, phosphatidyl ethanolamine, phosphatidyl inositol, phosphatidyl serine, phosphatidic acid and lysolecithines as well as mixtures thereof. Known products are Phoslipon®, for example. The contents of phospholipids ranges from 0.1 to 30 percent by weight, preferably 0.5 to 20 percent by weight.

The components (a) and (b) of the active substance preparation and the phospholipids (d) presumably form association-like configurations of different molecules which again are accumulated mostly homogeneously in the generating structure of the gel (c)+(e), the whole being called "association complex".

In combination with the cyclodextrins and the yeast decomposition product containing SOD, which product itself contains a number of different substances, a stable aggregation structure is formed within the gel, the structure of which aggregation/agglutination is not yet clear and the radical protection factor (explanation below) of which is considerably higher than the value to be expected by summarizing the individual values and which therefore brings about a synergy effect. It seems that the structure of the gel considerably influences the aggregation of the various substances and that it is probably the decisive factor as regards the stability of the aggregation.

The radical protection factor may be increased further by adding acerola extract and certain plant extracts.

According to the invention, the active substance preparation may also contain, in addition to the basic components (a) through (g), different plant extracts such as citrus peel or leaf extracts (*Citrus bigaradia, Citrus hystrix, Citrus aurantifolia, Citrofurtunella microcarpa, Citrus aurantium, Citrus reticulate*), petitgrain extract (peel or fruit), extract of the Spanish cherry, kiwi extract (*Actinidia chinensis*), papaya fruit-extract (*Caricae papayae*), tea extract [leaves of green or black tea, leaves or bark of new jersey tea (*Ceanthus velutinas*)], coffee bean extract (INCI name: coffee bean extract; of green or roasted beans), prunus extract (*Prunus armeniaca, Prunus dulcis, Prunus persica, Prunus domestica, Prunus spinosa, Prunus serotina, Prunus virginiana*), extracts of the bark of the Mexican skin tree (*Mimosa tenuiflora*), angelica root extract (*Angelica archangelica*). Such plant extracts are commercially available, e.g. from DRAGOCO, Holzminden; Germany.

The content of these plant extracts may range from 0 to 40 percent by weight, preferably from 0.1 to 40 percent by weight, in particular 1.5 to 20 percent by weight, where the mixture may also contain mixtures of these extracts as well as mixtures with acerola extracts in the active substance preparation.

Depending on the plant and the added quantity, the addition of the above plant extracts may increase the radical protection factor several times, presumably with the occurrence of synergistic interactions, the correlation between which we have not been able to find out yet completely.

Antioxidants that may be used in the invention include vitamins such as vitamin C and derivates of it, such as ascorbylacetates, phosphates and palmitates; vitamin A and its derivates; folic acid and its derivates, vitamin E and its derivates, such as tocopherylacetate; flavones or flavonoids; amino acids such as histidine, glycine, tyrosine, tryptophan and derivates thereof; carotinoids and carotenes, such as $\beta$-carotin, $\alpha$-carotin; uric acid and derivates; $\alpha$-hydroxy acids such as citric acid, lactic acid, malic acid; stilbenes and their derivates etc.

Vitamins may also be contained in a mixture with enzymes as another portion in the active substance preparation or in the cosmetic composition apart from the active substance preparation. The content may be at least be 0.5 percent by weight of a mixture of enzymes and vitamins containing at least 150 units/ml (U/ml) of superoxide dismutase (SOD).

Preferably, the used mixture of enzymes and vitamins is an ultrasound decomposition product of a yeast, where the decomposition product contains SOD, protease, vitamin $B_2$, vitamin $B_6$, vitamin $B_{12}$, vitamin $D_2$ and vitamin E. Preferably, it contains at least 150 U/ml of SOD, protease and the vitamins B and D, where the proportion between SOD and protease as international units at least ranges from 3:1 to 8:1.

Of special advantage for making the enzyme/vitamin mixture is an ultrasound-based decomposition method described in DE 4241154C1, where a cellular dispersion or suspension is passed through a continuous ultrasound irradiation cell, where the sonotrode protects up to half or two thirds of its length into the cell and is submerged in the medium to be exposed to ultrasound-irradiation. The sonotrode has an angle of 80.5 to 88.5 degrees, and the correlation between the submerged length in mm of the sonotrode and the exposed volume in ml is set to a value ranging from 1:1.1 o 1:20. The portion of solid particles in the medium to be exposed to acoustic irradiation ranges from 1:0.02 to 1:2.2 percent by weight.

Yeasts such as baker's yeast, brewing yeast, wine yeast as well as specially treated yeasts such as SOD-enriched yeasts can be used as cellular dispersions. For instance, a cellular dispersion that can be preferably used may contain Saccharomyces cerevisiae.

The addition, for instance, of 1 percent by weight of such a yeast decomposition product of baker's yeast or bio yeast as an optional portion of the aggregation structure with cyclodextrins may increase the radical protection factor, which itself is high already. Further remarks on the radical protection factor will be made below.

Commercially available $\alpha$-, $\beta$- and $\gamma$-cyclodextrins (Wacker-Chemie) or mixtures thereof may be used as cyclodextrins.

In addition to the above components the active substance preparation in the form of the association complex may also contain an extract of acerola fruits (*Malpighia punidifolia*). Acerola is a small tree indigenous to the West Indies, to northern South America, to Central America, Florida and Texas, which is rich in vitamin C and other active substances such as Vitamin A, thiamine, riboflavine and niacine, which may develop a complex activity together with different other components such as phosphor, iron, calcium. The aqueous acerola extract is normally available as a powdered product.

As another active substance in the complete composition of the cosmetic preparation and in addition to the above active substance complex an especially preferred embodiment may contain one or several of the following components:

(1) extracts or treated extracts of plants binding free radicals or moisture, selected among acerola fruits (*Malpighia punidifolia*), *Camellia oleifera, Colunsonia canadensis* and *Hibiscus sabdariffa;*

(2) extracts or treated extracts of algae binding free radicals or moisture, selected among omega plankton with a high content of cerebrosid stimulants, micro algae of the *chlorella* species and macro algae of the *ulva* species associated with byssus (mussel silk) as biotechnological protein fraction and subsequently associated with dextrine, wherein the product appears in the mixture with peptide derivates derived from α-MSH and associated with xanthin.

(3) natural and synthetic polymers selected among chitosanglycolate, condensed products of desiccated milk, and activated fatty acids, (4) magnetically hard single crystals of bariumhexaferrite having a coercitive field strength of 3000–5000 Oe and a grain size of 50–1200 nm intercalated in or mixed with asymmetric lamellar aggregates for phospholipids and fluorocarbons as well as (5) other active substances and carriers selected among hyaluronic acid, omega CH activator, behentrimonium chloride, passion flower oil as well as modified kaolin.

The mentioned modified kaolin is contained according to WO96/17588 and has been modified with spherical $TiO_2$ or $SiO_2$ particles having a size of <5 μm, wherein the spherical particles's share in the kaolin mixture ranges from 0.5 to 10 percent by weight. This is what makes the preparation feel very smooth on the skin and gives it additional anti-inflammatory functionality. The modified kaoline may amount to a content ranging from 0.1 to 6 percent by weight of the total quantity of the cosmetic.

The mentioned magnetically hard particles for stimulating the circulation of the blood may be such as described in WO95/03061 or such with smaller particle sizes and in a mixture with asymmetric lamellar aggregates charged with oxygen up to the saturation pressure, where the content of magnetic particles related to the total composition of the cosmetic may range from 0.01 to 10 percent by weight.

The mentioned asymmetric lamellar aggregates are known from WO94/00098 and consist of phospholipids and fluorocarbon charged with oxygen or a fluorocarbon mixture. The fluorocarbon content is in the range from 0.2 to 100 percent by weight/volume, wherein the phospholipid has a phosphatidyl choline content of more than 30 up to 99 percent by weight and where these aggregates have a skin penetration depending on the critical solubility temperature of the fluorocarbons.

In addition, the aggregates may also appear alone in the cosmetic preparation only charged with oxygen. The content may range from 2.5 to 20 percent by weight of the total composition of the cosmetic.

These aggregates are oxygen carriers and allow the penetration of the oxygen into the skin, thus improving oxygen supply to the skin.

The preparation according to the invention further contains cosmetic auxiliary substances and carriers as normally used in such preparations, e.g. water, glycerine, propylene glycol, preserving agents, colorants, pigments with colouring effect, thickeners, softening substances, moisture-preserving substances, aromatic substances, alcohols, polyalcohols, electrolytes, polar and non-polar oils, polymers, copolymers, emulsifiers, waxes, stabilisers. It is also advantageous to add suitable water-soluble and/or oil-soluble UVA or UVB filters or both to the composition according to the invention. Among advantageous oil-soluble UVB filters are 4-aminobenzoic acid derivates such as the 4-(dimethylamino) benzoic acid (2-ethylhexyl)ester, ester of the cinnamic acid such as the 4-methoxycinnamic acid (2-ethylhexyl)ester, benzophenone derivates such as 2-hydroxy-4-methoxybenzophenone, 3-benzylidene camphor derivates such as 3-benzylidene camphor.

Water-soluble UVB filters are for instance sulfonic acid derivates of benzophenone or of 3-benzylidene camphor or salts such as the Na or K salt of the 2-phenylbenzimidazol-5-sulfonic acid.

UVA filters include dibenzoylmethane derivates such as 1-phenyl-4-(4'-isopropylphenyl)propane-1,3-dione.

Preferred solar radiation protection filters are inorganic pigments on the basis of metal oxides such as $TiO_2$, $SiO_2$, $ZnO$, $Fe_2O_3$, $ZrO_2$, $MnO$, $Al_2O_3$, which can also be used as a mixture with each other or with organic filters.

Particularly preferred inorganic pigments are agglomerated substrates of $TiO_2$ and/or $ZnO$, with $SiO_2$ according to WO99/06012.

Particularly advantageously used $SiO_2$ particles are highly monodisperse, non-porous, spherical $SiO_2$ particles according to DE 3616133, produced by hydrolytic polycondensation of tetraalkoxy silane in an aqueous alcoholic-ammoniacal medium, where a sol of primary particles is generated, which subsequently brings the contained $SiO_2$ particles to the desired particle size of about 0.05 up to 10 μm by continuously adding tetraalkoxy silane proportioned in a controlled way, depending on the reaction.

Pigments, pigment mixtures or powders with pigment-like functionality, also comprising those having a pearlescent effect, may also comprise substances such as: mica, kaolin, talcum powder, mica-titanium oxide, mica-titanium oxide-iron oxide, bismuth oxychloride, nylon globules, ceramic globules, expanded and non-expanded synthetic polymer powders, powdery natural organic compounds such as pulverized hard algae, encapsulated and non-encapsulated cereal starches and mica-titanium oxide-organic dye.

Normally, a wide range of compounds may be used as softeners, such as stearyl alcohol, glyceryl monoricinoleate, glyceryl monostearate, 1,2-propanediol, 1,3-butandiol, cetylic alcohol, isopropyl isostearate, stearic acid, isobutyl palmitate, oleyl alcohol, isopropyl laurate, decyloleate, 2-octadecanol, isocetylic alcohol, cetylic palmitate, silicon oils such as dimethylpolysiloxane, isopropyl myristate, isopropyl palmitate, polyethylene glycol, lanoline, cacao butter, vegetable oils such as maize oil, cotton seed oil, olive oil, mineral oils, butyl myristate, palmitic acid etc.

Cosmetic preparations with the preparation of the active substance according to the invention may exist as O/W or W/o emulsions. Suitable emulsifiers for O/W emulsions are for instance addition products of 2–30 mol ethylene oxide to linear $C_8$–$C_{22}$ fatty alcohols, to $C_{12}$–$C_{22}$ fatty acids and to $C_8$–$C_{15}$ alkylphenols; $C_2$–$C_{22}$ fatty acid monoesters and diesters of addition products of 1–30 mol ethylene oxide to glycerine Glycerine monoesters and diesters as well as sorbitan monoester and diester of $C_6$–$C_{22}$ fatty acids, polyol- and polyglycerin-ester; addition products of ethylene oxide to castor oil; betaines such as coconut alkyl dimethyl ammonium glycinate or coconut acylaminoethylhydroxyethyl-carboxymethylglycinate (CTFA: cocamidopropyl betaines) as well as ampholytic tensides.

Suitable emulsifiers for W/o emulsions are for instance addition products of 2–15 mol ethylene oxide to castor oil, esters of $C_{12}$–$C_{22}$ fatty acids and glycerine, polyglycerin, pentaerythrite, sugar alcohols (e.g. sorbite), polyglucosides (e.g. cellulose), polyalkylene glycols, wool alcohols, copolymers of polysiloxan polyalkyl polyether.

The water content of a preparation with the active substance complex may vary within a wide range and is preferably between 5 and 90 percent by weight, where a lower water content of about 0.5–8 percent by weight may be found in particular in lipsticks.

The especially preferable cosmetic preparation with the active substance component (f) is a particularly effective protection against the attack of free radicals on the skin both alone and in combination with other active substances and has a surprising effect on the opening of the pores of the skin, similar to the effect of a cleaning means (peeling). This increases the efficiency of other properties by further ingredients of the cosmetic preparation, like improved moisturizing and smoothing of the skin, thus improving even more and for a longer time the entire state of the skin.

The preparation of the active cosmetic substance according to the invention, when applied either alone or in combination with other active substances, protects the skin in a particularly efficient way against the attack of free radicals on the skin. It has a high radical protection factor between 100 and $4500 \times 10^{14}$ Radicals/mg.

The radical protection factor (RPF) determines the activity of a substance for binding free radicals as compared with a test substance. The test substance consists of a highly reactive, semi-stable radical, which reacts with all known antioxidants. Such radicals include nitroxides such as proxo (2,2,5,5-tetramethyle-1-dihydropyrrolinoxy-nitroxide), tempol (2,2,6,6-tetramethyl-1-piperidinoxy-4-ol-nitroxide), DTBN (di-tert-butyl-nitroxide) or preferably DPPH (1,1-diphenyl-2-picryl-hydrazyl).

The RPF is determined by measuring the signal amplitude of the test radical by electron spin resonance (ESR/EPR) before and after mixing with an antioxidant and by calculating the RPF on this basis. For a series of standard antioxidants the RPF is a known parameter, so it is 827 for all-trans-retinole, 196 for all-trans retinal acetate, 41200 for DL-α-tocopherol and about 48 for α-tocopherol acetate, each $\times 10^{14}$ radicals/mg.

The preparation of the active cosmetic substance alone, if existing as "association complex" of the components (a) through (d) and the components (f) and (g) at a concentration of 10 percent by weight of (a) and (b) each has an RPF of 1255, which is very high as compared with common active substances in cosmetic formulations with declared radical scavengers, which achieve values of about 4 to 40. This is the case even though the concentration of the active substances themselves in (a) and (b) is only 2 percent by weight, as a maximum.

In (a) and (b), the really active substances are contained in a concentration of max. 2% by weight only. The component (e) further increases the radical protection factor by a certain value depending on its concentration. Surprisingly, this factor increases by another 1.3 to 10 times if the cyclodextrins are added, the radical protection factor of which is 0 (zero).

"High radical protection factor" according to the present invention means a value of 100 or higher, preferably 1000 or higher. In certain combinations of plant extracts and the association complex itself according to the present invention this value may be increased to 10000 and higher. Depending on the portion of the preparation, the corresponding cosmetic compositions with such preparations comprise radical protection factors, for example, from 40 to 400 or higher.

The exact method for measuring the radical protection factor has been described by Herrling, Groth, Fuchs and Zastrow in Conference Materials "Modern Challenges To The Cosmetic Formulation" 5.5.-7-5.97, Düsseldorf, p. 150–155, Verlag f. chem. Ind. 1997. Starting from the known concentration of the test substance (here: DPPH) or the number of its free radicals (radicals per ml) they measure a signal amplitude $S_1$ with an ESR spectrometer. The test radical and the antioxidant are dissolved in a water/alcohol solution (e.g. 0.1 m) each. The signal amplitude $S_2$ of the antioxidant is measured. The normalised difference between the two signal amplitudes is the reduction factor RF.

$$RF = (S_1 - S_2)/S_1$$

The result of the radical reduction of the test substance RC×RF is normalised relative to the quantity of product input PI (mg/ml). Where RC is the amount of the test substance, i.e. the known number of radicals in the test substance. The radical protection factor is calculated by means of the following equation:

The result is $$RPF = \frac{RC\ [\text{Radicals/ml}] \times RF}{PI\ [\text{mg/ml}]}$$

$$RPF = N \times 10^{14}\ [\text{Radicals per mg}],$$

where N is a positive real number and RPF for simplification may be reduced to the value of N. This reduction has been used in the examples of the present invention.

The radical protection factor may be determined by means of a handy and very simple ESR spectrometer (GALENUS GmbH, Berlin, Germany) and is a new magnitude for characterising cosmetic products as regards their capacity of binding free radicals. The method is an in vitro method, where no individual properties of the user of the cosmetic are influencing the antioxidants.

Other advantageous effects of products with the active substance preparation according to the invention, in combination with other active substances or carriers are a lasting improvement of the general state of the skin, a delayed ageing process of the skin, lasting improvement of the moisturizing and smoothing effect on the skin. The particularly advantageous embodiment described above with an additional algae-peptide product and magnetically hard single crystals of bariumhexaferrite comprises a special allergy-reduced risk, according to allergy and dermatological tests.

The cosmetic preparation according to the invention may be used, for example, in sun creams, sun gels, after-sun products, day creams, night creams, masks, body lotions, cleansing milk, makeup's, lipsticks, eye cosmetics, hair masks, hair conditioners, shampoos, shower gels, shower oils, bathing oils and other common products. Advantageous cosmetic preparations also include tooth pastes and mouthwash, under the special aspect of neutralising free radicals in the mouth of smokers and also as special cream for the hands and the face of smokers. Such products are manufactured in a way known by workers skilled in the art. When selecting special carrier substances, the corresponding pharmaceutical preparations may also be made.

Another subject matter of the invention is a cosmetic preparation comprising a content of plant extract selected from the group comprising Pongamia pinnata extract, tomatoe extract and mixtures thereof as has been defined more in detail above, with a content of 0.5 to 10 percent by weight as well as 99.5 to 90 percent by weight of other active substances or carriers or mixtures of active substances and carrier substances, each related to the total composition. Active and carrier substances may be the substances mentioned above.

The following examples are to illustrate the invention more in detail. If not otherwise indicated, all measures will be given in percent by weight.

Manufacture of the Active Substance Complex

For making the gel basis, gel powder such as carbomer was added to water, homogenised and subsequently neutralised with triethanolamine, for example. Then ethanol and glycerine were added to improve mixing properties, and the mixture was well stirred.

To this gel basis a mixture of phospholipids (Phoslipon®), Quebracho extract and silkworm extract was added and mixed at a temperature of up to 45° C. Then another portion of the above gel or a second gel such as Guar propyl triammonium chloride was added and stirred well with the whole mixture at increased temperature, but below 45° C.

Finally, the ultrasonic decomposition product and the cyclodextrin were added at a temperature of approximately 40° C. and while mixing thoroughly.

This way you got the active substance preparation according to the invention, hereinafter called "complex".

In those cases where the active substance preparation contained other ingredients such as acerola extract or extracts of tea, coffee, kiwi, citrus, cherry, papaya, tomato, Pongia pinnata or skin tree, such extract was added to the mixture of phospholipids and mixed with the gel.

EXAMPLE 1

Day cream phase A: carbomer 0.2; glycerine 2.0; propylene glycol 1,0; dist. water q.s. ad 100;
phase B: $C_{12}$–$C_{15}$-alkyl cetylic alcohol 3,7; stearate 0,5; jojoba oil 1,0;
phase C: triethanolamine 0,2;
phase D: active substance complex with (a) through (g) 3.5; preservant 0.3.

Phases A and B were warmed up to 65±2° C. while being stirred, and phase B was homogenised in phase A. Then phase C was added and homogenised correspondingly. Subsequently, the mixture was cooled down to 35° C. while being stirred, and phase D was added and mixed thoroughly. The active substance complex contained 1.0% of an SOD-containing enzyme/vitamin product obtained from baker's yeast using the ultrasound method according to DE 4241154C1.

The added active substance complex contained 1% of dry gel, 7% of phospholipids, 2% of Quebracho extract, 1% of silkworm extract, 1% of SOD from a yeast decomposition product, 2.5% β-cyclodextrin. The radical protection factor of this active substance complex amounted to 12215, and in the formulation the RPF was around 470.

COMPARATIVE EXAMPLE 1

A cosmetic composition was produced as described in Example 1, but wherein the complex of active substances did not contain dextrin. The complex of active substances had a radical protection factor of 1,925, the RPF of the formulation was 49.

EXAMPLE 2

Preparation Containing More Active Substances
Phase A: phospholipid 5.0; glycerine 8.0; ethanol 7.0; distilled water 2.0;
Phase B: Pongamia pinnata 2.0; tomato extract 5.0; extract of green tea 2.0; coffee extract 1.0;
Phase C: preservative 0.2; distilled water ad 100;
Phase D: carbomer 2.0; triethanolamine 2.0;
Phase E: complex of active substances containing (a) to (g) 5.0 (composition as in Example 1 except 3.4% β-cyclodextrin and 1.5% ultrasonic decomposition product of bio-yeast).

Phase A was produced by mixing (500–1,000 rpm) and homogenizing (10,000–30,000 rpm) the individual components at approximately 40° C. Phase B was produced by mixing (600 rpm) and homogenizing (30,000 rpm) the individual components at <40° C. Subsequently and also at a temperature of <40° C., phase C was added and homogenized (30,000 rpm), then phase D was added while stirring. Finally, the mixture was cooled down to approximately 35° C. and phase E was added while mixing thoroughly. Phase E had been obtained in a similar way as in Example 1. The complex of active substances (phase E) had an RPF of 7,380, the RPF of the formulation containing more active substances (phases A+B+C+D+E) was 9,870.

COMPARATIVE EXAMPLE 2

A cosmetic composition was produced as described in Example 2, but wherein the complex of active substances did not contain dextrin. The complex of active substances had an RPF of 7,380, the formulation containing more active substances had an RPF of 7,810.

The invention claimed is:
1. Cosmetic active substance preparation with a high radical protection factor, which comprises a content of
  (a) a product obtained by extraction of the bark of Quebracho Blanco and subsequent enzymatic hydrolysis, containing at least 90 percent by weight of proanthocyanidine oligomers and up to percent by weight of gallic acid, where the content of (a), which is available in a concentration of 2 percent by weight linked to a microcapsule ranges from 0.1 to 10 wt. %;
  (b) an extract of the silkworm obtained by extraction, containing the peptide cecropine, amino acids and a vitamin mix, where the content of (b) ranges from 0.1 to 10 wt. %;
  (c) a non-ionic, cationic or anionic hydrogel or mixture of hydrogels, where the content of (c) ranges from 0.1 to 5 wt %; and which is prepared by solution of a gel forming agent in water at temperatures above 40–50° C. and which hydrogel takes the gel structure at temperatures between 10 and 30° C.;
  (d) one or several phospholipids in the range of 0.1 up to 30 wt. %;
  (e) an ultrasound decomposition product of a yeast containing at least 150 units of superoxide dismutase per ml, wherein the content of the decomposition product is in the range from 0.5 to 4 percent by weight;

(f) one or more cyclodextrines selected from the group consisting of β- and γ-cyclodextrins with a share of 0.5 to 8% by weight; and (g) up to 100 percent by weight of water;

related to the total weight of the active substance preparation each.

2. Preparation according to claim 1, further comprising an extract of acerola fruits wherein the content, is in the range from 1 to 20 wt. %; related to the total weight of the active substance preparation, which extract is a powdered product stemming from an aqueous extract comprising vitamin C, vitamin A, thiamine, riboflavine, niacine, phosphorus, iron, calcium.

3. Preparation according to claim 1, wherein the portions of the components lie within the following ranges: active substance capsules according to (a) and (b) ranging from 0.5 to 3 wt. %, hydro gel according to (c) ranging from 0.1 to 3 wt. %, cyclodextrin and yeast decomposition product each in the range of 1 to 3% by weight.

4. Preparation according to claim 1, wherein a radical protection factor in the range from 100 to 3500, measured by determining the number of free radicals of a solution of a test substance (S1) by electron spin resonance (ESR) as compared with the ESR measurement result of the cosmetic active substance preparation according to the relationship $$RPF=(RC \times RF)/PI, \text{ where } RF=(S1-S2)/S1;$$
$RC$=concentration of the test substance (radicals per ml); $PI$=concentration of the active substance preparation (mg per ml).

5. Preparation according to claim 1, wherein the extract (a) contains at least 99 wt. % of proanthocyanidine oligomers and up to 1 wt. % of gallic acid.

6. Preparation according to claim 1, wherein the amino acids contained in (b) comprise aspartic acid, asparagine, threonine, serine, glutamic acid, proline, glycine, alanine, valine, cysteine, methionine, isoleucine, leucine, tyrosine, phenylalanine, lysine, histidine, arginine.

7. Preparation according to claim 1, wherein the active substance preparation contains portions of the components (a) and (b) each in the range of 0.1 to 3% by weight.

8. Preparation according to claim 1, wherein the active substance preparation exists as cosmetic composition, further comprising one or several of the following components:

(1) extracts or treated extracts binding free radicals or moisture of (1.1) plants selected among acerola fruits, *Camellia oleifera, Colunsonia canadensis* and *Hibiscus sabdariffa*; or (1.2) algae selected among omega plankton, providing a high portion of cerebrosid stimulants, microalgae of the *chlorella* species and macro algae of the *ulva* species associated with byssus (mussel silk) as biotechnological protein fraction and subsequently associated with dextrine, wherein the product appears in the mixture with peptide derivates derived from .alpha.-MSH and associated with xanthin;

(2) yeast decomposition products selected among baker's yeast, brewer's yeast, wine yeast and made according to a non-harming ultrasound treatment of the aqueous yeasts;

(3) natural and synthetic polymers selected among chitosanglycolate, condensed products of desiccated milk, and activated fatty acids;

(4) magnetically hard single crystals of bariumhexaferrite having a coercitive field intensity of 3000–5000 Oe and a grain size of 50–1200 nm intercalated in or mixed with asymmetric lamellar aggregates of phospholipids and fluorocarbons; and (5) other active substances selected among chitosanglycolate, hyaluronic acid, omega CH activator, behentrimonium chloride, passion flower oil and carrier substances;

(6) mixtures thereof.

9. Preparation according to claim 1, further comprising an additional portion of 0.1 to 20 wt. % of plant extracts which increases the free radical selected from the group consisting of citrus peel or leaf extracts of *Citrus bigaradia, Citrus hystrix, Citrus aurantifolia, Citrofurtunella microcarpa, Citrus aurantium*, or *Citrus reticulate*; peel or fruit extracts of petitgrain; extract of the Spanish cherry; kiwi extract; papaya fruit extract; extract of leaves of green or black tea; coffee bean extract of green or roasted beans; extract of *Prunus armeniaca, Prunus dulcis, Prunus persica, Prunus domestica, Prunus spinosa, Prunus serotina*, or *Prunus virginiana*); extracts of the bark of *Mimosa tenuiflora*; angelica root extract; *Pongamia pinnata* extract; and tomato extract; and the remaining portion of carrier substances or other active substances and carrier substances.

10. A cosmetic active substance as in claim 1, wherein said substance is in a form selected from the group consisting of a cream, a gel, a lotion, a mask, makeup, shampoo, a stick, an oil, mascara, a sun screen composition, a toothpaste and a mouthwash preparation.

11. A method for imparting to skin protection against free radical aggression, said method comprising applying to said skin a cosmetic active substance preparation which comprises a content of (a) a product obtained by extraction of the bark of *Ouebracho blanco* and subsequent enzymatic hydrolysis, containing at least 90 percent by weight of proanthocyanidine oligomers and up to 10 percent by weight of gallic acid, where the content of (a), which is available in a concentration of 2 percent by weight linked to a microcapsule ranges from 0.1 to 10 wt. %;

(b) an extract of the silkworm obtained by extraction, containing the peptide cecropine, amino acids and a vitamin mix, where the content of (b) ranges from 0.1 to 10 wt. %;

(c) a non-ionic, cationic or anionic hydrogel or mixture of hydrogels, where the content of (c) ranges from 0.1 to 5 wt %; and which is prepared by solution of a gel forming agent in water at temperatures above 40–50° C. and which hydrogel takes the gel structure at temperatures between 10 and 30° C.;

(d) one or several phospholipids in the range of 0.1 up to 30 wt. %;

(e) an ultrasound decomposition product of a yeast containing at least 150 units of superoxide dismutase per ml, wherein the content of the decomposition product is in the range from 0.5 to 4 percent by weight;

(f) one or more cyclodextrines selected from the group consisting of β- and γ-cyclodextrins with a share of 0.5 to 8% by weight; and (g) up to 100 percent by weight of water;

related to the total weight of the active substance preparation each.

12. A method as in claim 11, wherein said cosmetic active substance preparation is in the form of a cream, a gel, a lotion, a mask, makeup, shampoo, a stick, an oil, mascara, a sun screen composition, a toothpaste and a mouthwash.

* * * * *